US005383894A

United States Patent [19]

Dye

[11] Patent Number: 5,383,894

[45] Date of Patent: Jan. 24, 1995

[54] COMPRESSION DEVICE HAVING STEPPER MOTOR CONTROLLED VALVES

[75] Inventor: John D. Dye, Bridgewater, Mass.

[73] Assignee: The Kendall Co., Mansfield, Mass.

[21] Appl. No.: 99,506

[22] Filed: Jul. 30, 1993

Related U.S. Application Data

[63] Continuation-in-part of Ser. No. 790,809, Nov. 12, 1993, abandoned.

[51] Int. Cl.$^{6}$ .............................. A61B 17/12

[52] U.S. Cl. .............................. 606/201; 606/202; 606/204

[58] Field of Search .............................. 606/201, 202, 204

[56] References Cited

U.S. PATENT DOCUMENTS 4,738,249 4/1988 Linman et al. .................... 128/24 R
4,770,181 9/1988 Tomoda .............................. 128/648
4,838,257 6/1989 Hatch ............................... 128/204.18

FOREIGN PATENT DOCUMENTS 2104684 3/1983 United Kingdom .

*Primary Examiner*—David A. Wiecking
*Assistant Examiner*—John S. Hilten
*Attorney, Agent, or Firm*—Alvin Isaacs

[57] ABSTRACT

A compression device for applying compressive pressures against a patient's limb through means of a flexible, pressurizable sleeve which encloses a limb. The compression device has a pressure control apparatus which includes a microprocessor, a driver circuit and a flow control valve having a stepper motor attached thereto. The microprocessor is programmed to control pressure to the sleeve in conjunction with the driver circuit and the flow control valve by actuating the stepper motor. The microprocessor compares a signal generated by a pressure transducer to a preselected pressure value, it then generates an electrical signal to a driver circuit which in turn sends pulses to the stepper motor to automatically adjust the flow control valve, thus, controlling the flow of fluid therethrough so as to maintain a preselected pressure applied to the limb by the pressure chamber of the sleeve.

5 Claims, 3 Drawing Sheets

COMPRESSION DEVICE HAVING STEPPER MOTOR CONTROLLED VALVES

This application is a continuation-in-part of application Ser. No. 07/790,809, filed Nov. 12, 1993 and now abandoned.

BACKGROUND OF THE INVENTION

1. Field of the invention

The present invention relates to a device for applying compressive pressures against a patient's limb through means of a compression sleeve enclosing the limb, and more particularly, to a means for automatically adjusting the pressure applied to the sleeve to maintain a preselected pressure and to eliminate any application of excessive pressures to the limb.

2. Description of the Prior Art

Compression sleeves and devices for controlling them are well know and illustrated in the prior art in such patents as U.S. Pat. No. 4,013,069 of Hasty; U.S. Pat. No. 4,030,488 of Hasty; U.S. Pat. No. 4,091,804 of Hasty; U.S. Pat. No. 4,029,087 of Dye et al; U.S. Pat. No. 3,942,518 of Tenteris et al; and U.S. Pat. No. 2,145,932 of Israel, and reference may be had thereto for general background information on structure and utility.

Flexible compressive sleeves having a plurality of pressure compartments/chambers are wrapped around the limb of a patient and are then pressurized to apply compressive pressure to different parts of the limb. The sleeves are connected to a source of pressurized fluid which is regulated by a controller. The controllers generally operate to form pressure cycles which propel the blood upwards from the ankle towards the thigh.

Such devices can be misadjusted or drift from proper adjustment so that safe and effective pressure may not be applied to the limbs.

Prior art such as U.S. Pat. No. 4,396,010, of Arkans, U.S. Pat. No. 4,702,232, of Gardner, and U.S. Pat. No. 4,013,069, of Hasty, incorporated herein by reference, manually control the amount of pressure that is to be supplied to a patient's limb. Furthermore, although Arkans provides a method of depressurizing a pressure compartment by use of a pressure release device, Arkans method of controlling the pressure applied to the limb is still provided by a manual control.

Other prior art, such as GB 2104684 A of Thomas Mummeft, provides an electronic control circuit for regulating a dynamic pressure wave pneumatic control system, which in essence controls the activation and de-activation of solenoid valves so as to regulate the inflation and deflation of a sleeve in place around an extremity of a patient. The main components of this control circuit are comparators and a sleeve inflation dampener. The sleeve inflation dampener is a pneumatically-restrictive device typically spring actuated for regulating the flow of therethrough at a predetermined rate to a sleeve. The comparators are responsive to a predetermined pressure level signal and a transducer signal and generate control signals to solenoids which activate solenoid, and valves regulate the pneumatic control circuit. Each comparator generates a low signal when the signal from the appropriate level set unit (level set units are composed of individually adjustable voltage-dividing components) is greater than the amplified signal from a sleeve pressure transducer. Each comparator generates a high signal when the amplified signal from a sleeve pressure transducer is greater than or equal to the signal from the appropriate level set unit. The output of the comparators is connected to solenoids, so that when a solenoid receives a low signal from a comparator it will de-energize and its valve will close, and when a high signal is received the solenoid will be energized and its valve will be in an open position. The pneumatic flow from the air supply is thusly conducted to the sleeve at a rate controlled by the sleeve inflation dampener, a spring actuated device. So in essence, the control circuit of the prior art simply opens or closes solenoid valves to permit air flow therethrough to the sleeve dampener to control air flow to the sleeve. The sleeve dampener being spring actuated must be preset to permit a fixed amount of air flow to the sleeve. And, because the solenoids are either opened or closed there is no in between setting.

This is not the case with the present invention. The present invention is a distinct improvement over the prior art because a microprocessor is used in conjunction with a computer program to automatically control a flow control valve attached to a stepper motor resulting in continuous regulation of fluid flow to the pressure sleeve. The microprocessor manipulates the flow control valve to provide just the right pressure to a sleeve that is around the extremity of a patient.

Even though the prior art has accomplished the depressurizing of chambers to reduce injury to a patient's limb, the control of the pressure supplied to the pressure compartments is still very inefficient and leaves much to be desired. Thus, a nurse or operator must remain with the unit constantly until the pressure has come to a preselected value and then must frequently check and recheck the pressure unit to make sure the pressure setting remains steady. Additionally, changes in the patient's position cause changes in the effective volumes of the pressure chambers resulting in undesirable changes in the pressures in the individual pressure chambers which requires further manual adjustment. The present invention provides a constant pressure to this sleeve irrespective of the position of the patient.

The aforementioned prior art attempts to precisely control pressure applied to a patient's limb but falls short of its expectations. The reason for this failure is the inherent restrictions of the components of the apparatus used. Systems that rely on the opening and closing of solenoids to control the flow of pressure are antiquated and lag behind current technology. The present invention has advanced the art of pressure control to precisely and automatically control pressure delivered to a pressure chamber of a sleeve.

A need exists for automatic control over application of a preselected pressure to the pressure chambers of a sleeve so that that preselected pressure value is maintained, and the time required by a person to watch over a pressure monitor is further reduced. The present invention provides such an automatic control to control pressure exerted on a patient's limb.

SUMMARY OF THE INVENTION

The present invention is a compression device for applying compressive pressures against a patient's limb through means of a flexible pressurizable sleeve which encloses the limb. The device has a pressure control apparatus which includes a microprocessor, a driver circuit and a flow control valve having a stepper motor attached thereto. The microprocessor is programmed to control pressure to the sleeve in conjunction with the driver circuit and flow control valve by actuating the stepper motor attached to the flow control valve. The microprocessor generates an electrical signal to the drive circuit which in turn sends pulses to the stepper motor to automatically adjust the flow control valve. The flow control valve acts to control the flow of pressurized fluid to the sleeve so as to maintain a preselected pressure applied to the limb by the pressure chamber of the sleeve.

The object of the present invention is to provide a compression device that has a pressure control apparatus for controlling the application of compressive forces against a patient's limb through a flexible pressurizable sleeve which encloses the limb with the pressure control apparatus automatically adjusting pressure supplied to a pressurized sleeve to maintain a preselected pressure value.

Another object is to provide automatic pressure adjustment to eliminate the need for a nurse or similar person from having to continuously monitor the pressure selection to insure it remains at a preselected pressure value.

Another object of the present invention is to provide automatic pressure adjustment in response to changes in the effective volumes of the pressure chambers of the sleeve caused by changes in a patient's position.

Other objects will become more apparent from the following description of the preferred embodiment and claims.

DESCRIPTION OF THE PREFERRED EMBODIMENT

Figure 1:
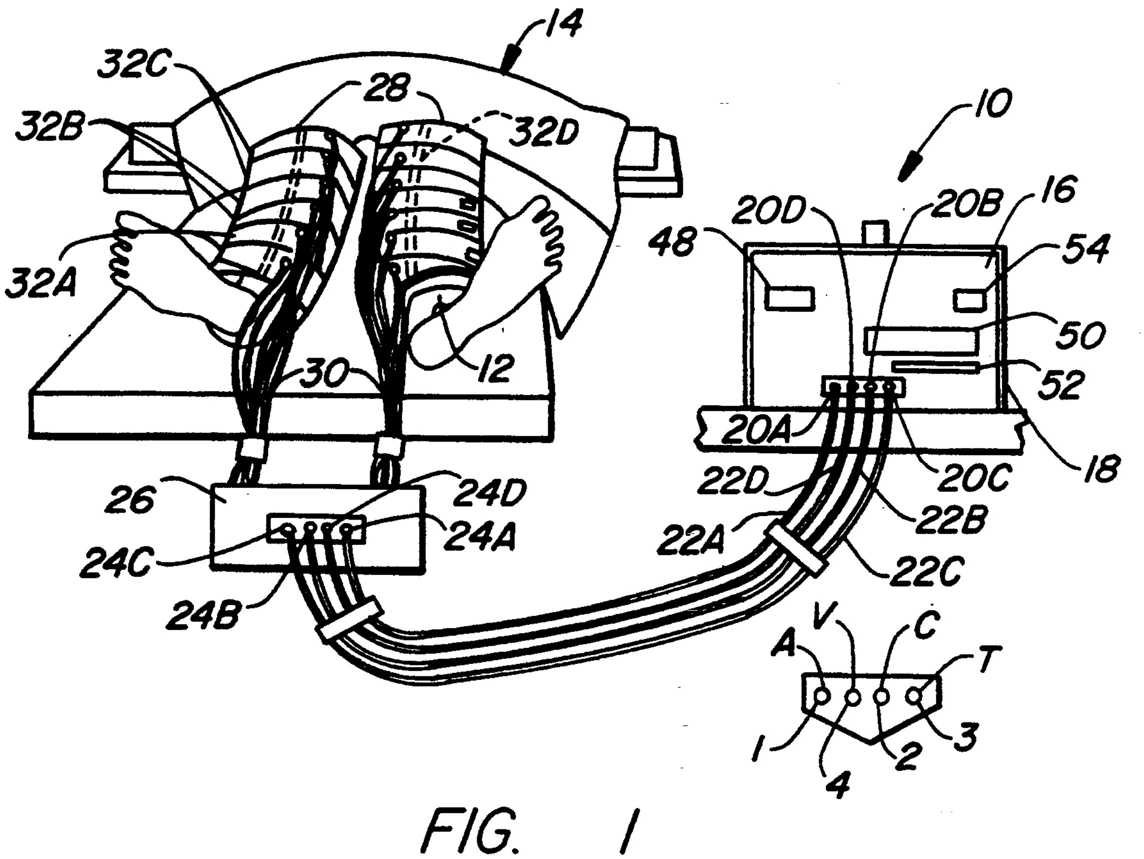
FIG. 1 is a perspective view of the sequential compression device used to apply compressive forces to the legs of a patient.

Referring to FIG. 1 and to briefly describe the compressive device, the compression device 10 is seen as supplying sequential compressive pressures and cooling to legs 12 of a patient 14.

Figure 2:
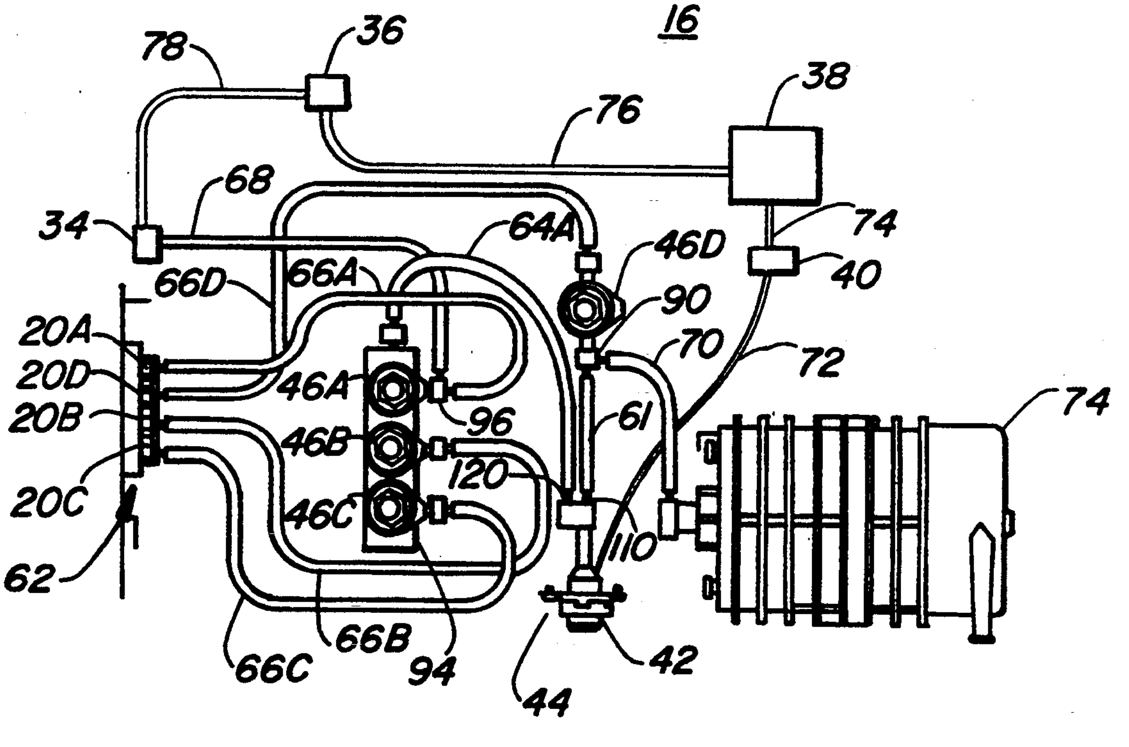
FIG. 2 is a schematic diagram, partially in block form, showing the preferred embodiment.
Figure 3:
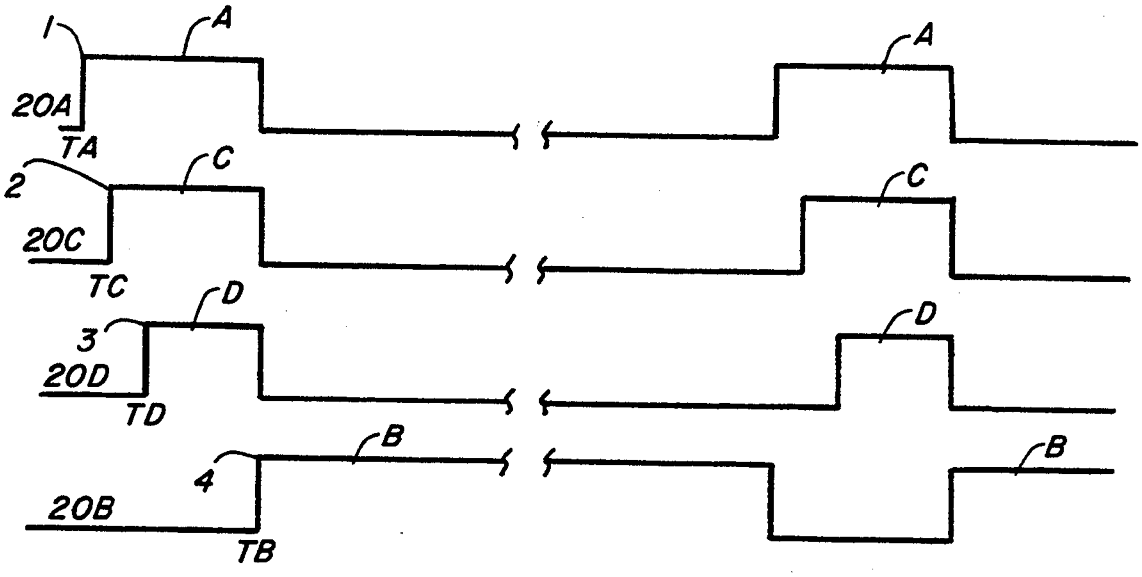
FIG. 3 is a timing diagram of the pressure cycles.

The device 10, as shown in FIG. 2., includes an air compressor 74, solenoid valves 46A, 46B and 46C in a solenoid manifold 94, a solenoid valve 46D for venting of air, a pressure transducer 34, a signal converter 36, and a pressure control apparatus 16, which incorporates a microprocessor 38, a driver circuit 40 and a flow control valve 44, mounted in a case 18. The air compressor 74, generates the pressures timed as illustrated in FIG. 3, at output ports 20A, 20C, 20D and 20B, respectively. The output ports 20A–20D are connected through flexible tubes 22A, 22B, 22C, and 22D and are in fluid communication with input ports 24A, 24B, 24C, and 24D of a manifold 26. Two sets of input ports are connected to a pair of compression sleeves 28 by a pair of flexible sets of tubes 30.

The compression sleeves 28 are identical to each other. And as shown in FIG. 1, each is wrapped around one of the patient's legs 12. Each sleeve has three pressure chambers 32A, 32B, and 32C. In addition, each sleeve has one or more ventilation chambers 32D for ventilating the patient's legs 12. The sleeves are of the same type shown in U.S. Pat. No. 4,396,010, of Arkans, and other patents referenced therein.

Referring to FIG. 2, there is shown a pressure control device 16, which includes a microprocessor 38 that functions to repetitively generate pressure pulses to output ports 20A–20D in the time sequence shown by wave-forms of FIG. 3. As seen by FIG. 3, the pressure cycles commence at time TA when pressure pulse A is applied to port 20A and the ankle chambers 32A are pressurized. At time TB, pressure pulse B is applied to port 20C and the calf chambers 32B are pressurized. At time TO, pressure pulse C is applied to port 20C and the thigh chambers 32C are pressurized. At time TD, pressure pulses A, B, and C are terminated, chambers 32A, 32B and 32C are vented to the atmosphere, and cooling pulse D is applied to port 20D and ventilation chambers 32D. At the end of the cooling pulse, the entire sequence is repeated commencing with pressure pulse A.

Referring to FIG. 2, there is shown a compressor 74 as a generating source of pressurized fluid. The compressor 74 is connected through a pneumatic connection 70 to fluid junction 90 which is connected to solenoid valve 46D and the inlet opening 110 of flow control valve 44 through pneumatic connection 61. The discharge opening 120 of flow control valve 44 is connected through pneumatic connection 64A to the solenoid valve manifold 94. The solenoid valves 46A, 46B, 46C and 46D control the input of pressure, by being opened or closed, through pneumatic connections 66A, 66B, 66C, and 66D to a manifold 62 which has output ports 20A, 20D, 20B, and 20C. The pressure transducer 34, of a commercially available type, is in fluid communication with the solenoid manifold 94 through pneumatic connection 68 and fluid junction 96.

The pressure transducer 34 senses the pressure at output port 20A through pneumatic connection 66A and converts the pressure sensed into a first electrical signal. The first electrical signal is an analog electrical signal and is communicated to a signal converter 36 through lead 78. This first electrical signal is received by the signal converter 36, of a commercially available type, which converts the analog electrical signal to a digital electrical signal. The digital electrical signal generated by the signal converter 36 is then communicated to the microprocessor 38 through lead 76. The digital signal is received by the microprocessor 38. The microprocessor 38 has a specifically designed computer program which permits the microprocessor to monitor and compare the digital signal from the signal converter to a preselected pressure value programmed into the microprocessor and set by the microprocessor's program. The microprocessor's program compares the digital signal against the microprocessor's preselected pressure value. If the pressure sensed by the transducer is the same as the microprocessor's preselected pressures, no electrical signal is sent by the microprocessor to the driver circuit to correct the pressure being supplied to the sleeve. However, if the pressure sensed by the transducer does not match the preselected value of the microprocessor, then the microprocessor 38 sends a second electrical signal to a driver circuit 40, of a commercially available type, through lead 75 which emits pulses of current through lead 72 to a stepper motor 42. The stepper motor 42 is a linear stepper motor which is attached to and integral with flow control valve 44. This combination of valve and stepper motor was designed especially for the present invention. The valve was designed by the Kendall Company of Mansfield, Mass., and is made by Kaysun Inc. of Wisconsin. The stepper motor is provided by Air Pacs of Connecticut. The microprocessor 38 sends pulses to the stepper motor 42 which activate the flow control valve 44 which in turn controls the flow of fluid to solenoid valves 46A, 46B, and 46C. Thus, the pressure applied to outlet ports 20A–C through solenoid valves 46A–C is dynamically regulated by the microprocessor which automatically adjusts the flow of pressurized fluid through the flow control valve 44.

Figure 4:
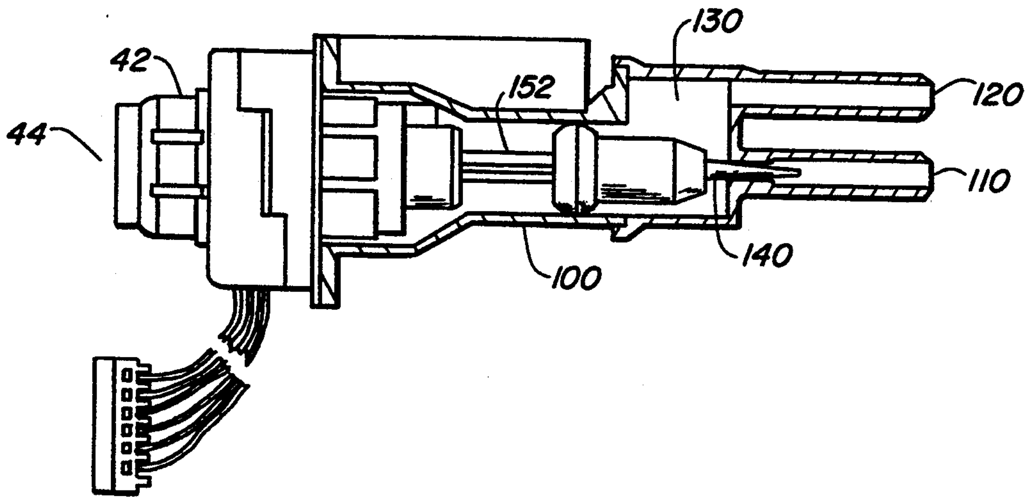
FIG. 4 illustrates the flow control valve used to control the flow of fluid to solenoid valves.

Referring to FIG. 4, flow control valve 44, is a major part of the means of the controlling and automatically adjusting the pressure in pressure sleeves is depicted. The valve has a hollow body member 100 which has an inlet opening 110, and a discharge opening 120 therein. The body member 100 also has a chamber 130 in communication with the inlet and discharge openings. The chamber 130 is cylindrical in shape. The body member 100 may be made from any type of material such as aluminum, steel, brass, etc., although the preferred material is plastic. The flow valve also has a means for sealing against fluid flow entering the chamber 130, the means including a tapered member 140 for releasably seating into the inlet opening 110. The tapered member 140 may be made of several materials, such as steel, aluminum, other metals or composites. The preferred material is brass because of ease of movement. The tapered member 140 is in slideable contact with the upper most wall of the cylindrical chamber 130. The taper of the tapered member 140 is a compound taper which permits the tapered member 140 to precisely control the flow of fluid through the inlet opening 110. Attached to the hollow body 100 is a means for moving the tapered seating member 140. This means is a linear stepper motor 42. The tapered member 140 is connected to a shaft 152 of the motor 42 which extends into the hollow body 100. The motor moves the tapered member 140 in a linear motion in and out of the inlet opening 110. The stepper motor 42 provides linear motion in increments of 2 hundredths of an inch. In addition, the motor 42 has a predetermined internal stop to prevent the tapered member 140 from jamming into the body of the motor. There is also a predetermined internal stop to prevent the tapered member 140 from jamming into the inlet opening 110. Because the stepper motor 42 is calibrated to move in increments of 2 hundredths of an inch, it can move the tapered member precisely into and out of the inlet opening 110 without causing it to jam. Furthermore, because the tapered member 140 has a compound taper, the flow of fluid into the inlet opening 110 can be precisely controlled, thereby providing finite adjustments in the flow of fluid to the solenoid valves and therefore to the compression chambers.

The flow of fluid is precisely controlled due to the combination of the incremental movement of the tapered member 140, the compound taper of the tapered member, and the stepping of the stepper motor by the pulses sent to the motor by the driver circuit. As the tapered member 140 is being moved into position for seating in the inlet opening 110, the compound tapered member reduces the area around the inlet opening 110 incrementally until it eventually seats in the inlet opening. This combination permits the finite pressure adjustments. As the tapered member is moved in or out of the inlet opening, the area between the taper and the inlet opening diminishes or expands, thus, exact control over the pressure flowing through the flow valve is had, which is necessary to maintain a preselected pressure.

Figure 5:
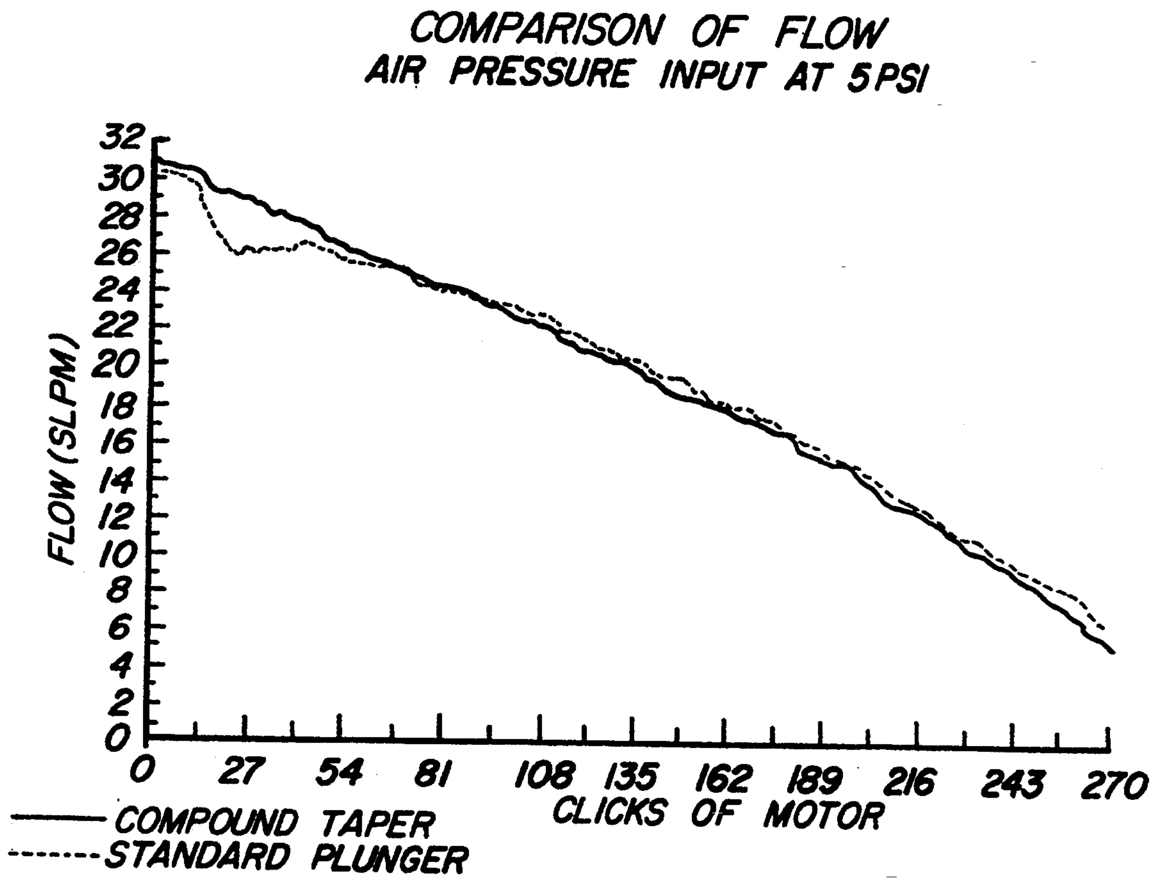
FIG. 5 is a flow vs plunger position chart.

The control of the pressure by the valve and stepper motor is illustrated in FIG. 5 wherein a comparison is made of the present invention compound taper and a standard plunger commonly used within flow control valves. The difference in the slopes of pressure is quite obvious. The slope of the pressure when using the standard plunger dips downward showing a pressure drop has occurred. On the other hand, the pressure slope of the present invention is stable and has no substantial pressure drops in its slope. This is important when providing pressure to a pressure sleeve that is being used on the limb's of a patient because any drop in pressure may cause the compressor supplying the pressure to over compensate and provide to much pressure which may possibly cause injury to the patient. By using this new valve there are no pressure drops, thus when the microprocessor sends pulses to the stepper motor, the motor in turn either moves the valve progressively to an open position or an incremental open position or a closed position depending on the flow of fluid needed to maintain the microprocessor's preselected pressure. The valve in conjunction with the stepper motor and the microprocessor automatically adjusts the pressure in the pressure sleeves, and an even flow of pressure will be assured without the compressor providing unneeded pressure to the sleeves.

As stated in an earlier paragraph, the stepper motor and flow control valve were designed specifically to be used as part of the pressure control apparatus to automatically control pressure to the sleeves by using a linear stepper motor to move a tapered member (plunger) in a linear motion in a precise manner. Prior art motors were of the constant rotary motion type and would turn the plunger down and up by screwing it into position. This has its disadvantages because if the rotary movement of the motor is not controlled, the rotary motion would exert a substantial force between the inlet and the plunger when seating the plunger so as to cause it to jam and not permit the plunger to be retracted. Although the rotary motion or movement of a rotary motor may be controlled it may not be controlled as precise as a linear stepper motor. Furthermore, the cost to do so is prohibitive and thus, economically unsound for use in this art.

Referring once again to FIG. 1, the pressure control apparatus 16 along with the other components is mounted in a case 18, the case having various controls and indicators. A Setting LED (light emitting diode) 48 is provided to indicate the preselected pressure that is to be applied to the chambers 32A, 32C, 32D, of the sleeves. A cycle monitor 50 is also provided to continuously display the status of the controller's compression sequence. The cycle monitor 50 consists of four back lit panels, which when lighted read: ANKLE, CALF, THIGH, and VENT. These represent the four major divisions of one complete cycle. During operation, the ANKLE, CALF, THIGH and VENT lights will light, one at a time, to indicate each of the major cycle divisions in turn. In addition, there is a ten-segment bar graph 52. Each of the ten segments of the bar represents ten percent of a major cycle division and will light in sequence to indicate how much of a major cycle division is complete. There is also provided a Run LED 54 which indicates that the actual pressure is within 2 mmHg of the set pressure.

At start-up, the microprocessor's program sets the setting LED 48 at 45 mmHg and displays as the set pressure. The setting LED 48 will light indicating that the microprocessor's 38 program is in the process of adjusting the actual pressure being supplied by the compressor 74. Within four cycles, the setting LED 48 will turn off and the Run LED 54 will come on, indicating that the actual pressure is within 2 mmHg of the set pressure. The microprocessor 38 will continue to operate to make small adjustments in order to more perfectly match the set pressure.

The microprocessor 38 of the pressure control apparatus 16 controls pressure to the sleeves by automatic pressure adjustment, it not only sets the pressure automatically but maintains the set pressure no matter how the patient moves or changes position.

To further explain the pressure control apparatus 16, the following is a description of the feedback loop used to control sleeve pressure by using a microprocessor programmed to determine sleeve size and then changing the control algorithm based upon that determination. Upon startup, the microprocessor's program has a default pressure of 45 mmHg as the reference pressure (henceforth called the "set pressure").

The microprocessor is programmed, so when start-up commences, to send an electrical signal to a driver circuit which sends a series of pulses to the stepper motor to close a flow control valve attached thereto. (each pulse moves the stepper motor 0.002 inches. This is a consistent and repeatable response to pulses from the microprocessor). In operation, it requires 256 steps to close the flow control valve from the fully open position. This number is used to insure the valve is closed fully regardless of it's initial position.

Once the valve is closed, the microprocessor is programmed to send pulses to open the flow control valve to a predetermined position, which is 73 Steps or 0.146 of an inch, for the first inflation cycle.

At the end of the compression portion of the cycle, the microprocessor's program takes the last pressure (actual Pressure) before the start of the vent phase of the cycle and uses it to compare to the set pressure (reference pressure). If this pressure is 13 mmhg greater than the set pressure, small sleeve subroutine is used. If the actual pressure is not 13 mmhg greater than the set pressure, the standard sleeve subroutine is used. The microprocessor is programmed to have both a standard sleeve subroutine and a small sleeve subroutine.

If the standard sleeve subroutine is used, the actual pressure is compared to the set pressure by the microprocessor's program and based upon the magnitude of the error, the microprocessor sends a series of pulses to either open or close the flow control valve. For each mmhg of pressure error the flow valve is moved 3 steps. For example, if the initial pressure was 51 mmhg, this would represent a 6 mmHg error from the default pressure. The microprocessor would then send 6×3 pulses for 18 pulses) to close the valve 18 steps (0.036 inches). The microprocessor then waits for the completion phase of the cycle. At the end of the next compression, the last reading prior to the vent portion of the cycle is again compared to the set pressure. If the pressure was 42 mmHg, for example, the microprocessor would send 9 pulses to open the valve 0.018 inches. (the error is 3 mmHg, 3×3=9). If the error after the next compression was 1 mmHg, or 46 mmHg, the stepper motor would close the flow control valve 3 steps, and, at the same time, (because the error was 2 mmHg or less) the Setting Light would be turned off, and the Run Light would be turned on. Also, (because the error was 2 mmHg or Less) various alarms that had been turned on would be disarmed. (If the controller continued to have 5 compression's on one side of the set pressure, a fault condition would be tripped). The microprocessor is programmed to continue to make corrections until the error is 0.2 mmHg or less or whenever the error should become greater than 2 mmHg.) If the small sleeve subroutine is selected by the microprocessor, the same routine is used, except all the correction pulse numbers are divided by two. Prior to the completion of the first compression phase of the cycle, if the set pressure is changed by an operator pressing either the UP or Down arrows, the valve stepper motor is pulsed one pulse for each mmhg moved. After the first compression, the stepper motor is pulsed 3 times for each mmhg or alternating one and two pulses if the small subroutine is used.

With the advent of the present inventions automatic pressure adjustment, manual control is not required to adjust the pressure to the chambers during the pressure cycle, therefore, all aspects of manual control have been removed along with the antiquated method of controlling the flow of pressure by the sole use of opening and closing solenoid.

The automatic adjustment feature of the present invention provides a significant advancement and a tremendous achievement over the prior art, therefore an advantage over all prior art. Because the present invention automatically adjusts the pressure to pressure chambers in a sleeve, the requirement to have someone constantly watch over a pressure monitor to see the rise in pressure, and then to have them continue to monitor the pressure to make sure the pressure does not exceed a preselected pressure or to make sure that the chambers have not been depressurized during the pressure cycle because of overpressurizing the chambers, has been eliminated. The nurse can start the pressure generating device, which has a preselected pressure and go on to other duties. The microprocessor will monitor the pressure being supplied to the pressure chambers in the sleeve and will automatically adjust the pressure until the required pressure is arrived at. The microprocessor will then continue to monitor the pressure provided throughout a pressure cycle and maintain the preselected pressure without having to manually make adjustments. The time saved by not requiring constant monitoring is substantial and makes it economically sound for use in hospitals or even in the home where costs might be prohibitive to a user.

The present invention, even though automatically adjusting the pressure delivered to pressure chambers, also has a means, as does prior art, to depressurize the pressure chambers in the sleeves, either when the last pressure cycle has terminated, as suggested in an earlier paragraph, or in case of an involuntary shut down or overload of the pressure system.

A description is given of the present invention for clarity and understanding and no limitations are to be considered other than those proposed by the specification and claims thereof.

What I claim is:

1. A compression device for applying compressive pressure against a patient's limb comprising:

a source of pressurized fluid, a flexible sleeve enclosing the limb with at least one pressure chamber connected to the source, at least one solenoid valve connected to the source and connectable with the pressure chamber, a pressure transducer connectable to the solenoid valve for transforming pressure it senses from the source to an analog signal, a signal converter for converting the analog signal to a digital signal, and a pressure control apparatus for receiving the digital signal;

a microprocessor programmed to monitor and adjust pressure to a sleeve pressure chamber, the microprocessor being programmed to have a preselected pressure value, to receive the digital signal from the signal converter, to compare the digital signal to the preselected pressure value, and after the comparison to send an electrical signal, if needed, for controlling pressure to the sleeve;

a driver circuit for receiving the electrical signal from the microprocessor, the driver circuit then emitting electrical pulses to further control pressure to the sleeve; and a flow control valve having a stepper motor attached thereto connectable between the source of pressurized fluid and said at least one solenoid valve, the stepper motor being responsive to the electrical pulses emitted by the driver circuit for controlling the flow control valve so as to adjust the pressure being delivered to the pressure chamber by precisely regulating the fluid flow through the flow control valve to said at least one solenoid valve permitting the flow of fluid to the sleeve pressure chamber.

2. The device of claim 1 wherein the stepper motor is a linear stepper motor.

3. The device of claim 1 wherein the flow control valve for controlling and automatically adjusting pressure to sleeve pressure chamber comprising;

a hollow body member having an inlet opening and a discharge opening therein, and a chamber in communication with said inlet and discharge openings;

a means for sealing against fluid flow entering said chamber said means including a tapered member for releasably seating into said inlet opening; and means for moving said tapered member said means including a linear stepper motor for moving said tapered member in a linear motion.

4. The flow control valve of claim 3 wherein said linear stepper motor is calibrated to move in a linear motion in increments of at least 0.002 of an inch.

5. The flow control valve of claim 3 wherein said taper of said tapered member is a compound taper.

* * * * *